United States Patent
Rozovsky et al.

[11] 4,363,750
[45] Dec. 14, 1982

[54] CATALYST FOR DEHYDROGENATION OF OXYGEN CONTAINING DERIVATIVES OF THE CYCLOHEXANE SERIES INTO CORRESPONDING CYCLIC KETONES AND/OR PHENOLS

[76] Inventors: Alexandr Y. Rozovsky, Rublevskoe shosse, 97, korpus 3, kv. 25; Valentin D. Stytsenko, ulitsa Musy Dzhalilya, 34, korpus 2, kv. 18; Svetlana A. Nizova, ulitsa Volgina, 27, kv. 144; Petr S. Belov, ulitsa Vavilova, 52, korpus 3, kv. 163; Alexandr J. Dyakonov, ulitsa Begovaya, 32, kv. 71, all of Moscow, U.S.S.R.

[21] Appl. No.: 223,073

[22] Filed: Jan. 7, 1981

[51] Int. Cl.³ .................. B01J 23/82; B01J 23/78
[52] U.S. Cl. .................. 252/459; 252/443; 252/473
[58] Field of Search ............. 252/459, 473, 443

[56] References Cited

U.S. PATENT DOCUMENTS 2,137,101  11/1938  Spicer ..................... 252/459 X
3,692,701   9/1972  Box, Jr. et al. ........... 252/473 X

FOREIGN PATENT DOCUMENTS 2129834  12/1971  Fed. Rep. of Germany ...... 252/473

*Primary Examiner*—Carl F. Dees
*Attorney, Agent, or Firm*—Ladas & Parry

[57] ABSTRACT

A catalyst for dehydrogenation of oxygen-containing derivatives of the cyclohexane series of the general formula:

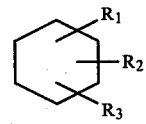

wherein $R_1$ is hydrogen or a $C_1$–$C_4$ alkyl; $R_2$ and $R_3$ are radicals having the same or different meanings: —H, —OH, =O, provided that $R_2$ and $R_3$ are not simultaneously hydrogen and $R_1$, $R_2$ and $R_3$ are attached to different carbon atoms of the cycle, into the corresponding cyclic ketones and/or phenols containing the following components, percent by weight:

| | |
|---|---|
| nickel | 15 to 55 |
| promotor-germanium and/or lead | 0.2 to 8.0 |
| inert carrier | 84.8 to 37.0 | and an atomic ratio of nickel to the promotor is within the range of from 15:1 to 410:1 respectively. The catalyst can additionally contain a salt of an alkali metal and a mineral acid in an amount of from 0.01 to 1.0% by weight.

3 Claims, No Drawings

CATALYST FOR DEHYDROGENATION OF OXYGEN CONTAINING DERIVATIVES OF THE CYCLOHEXANE SERIES INTO CORRESPONDING CYCLIC KETONES AND/OR PHENOLS

The present invention relates to the art of catalytic reactions of organic compounds and, more specifically to catalysts for dehydrogenation of oxygen-containing derivatives of the cyclohexane series into corresponding cyclic ketones and/or phenols and to processes for dehydrogenation of oxygen-containing derivatives of the cyclohexane series into corresponding cyclic ketones and/or phenols which stipulate the use of such catalysts.

Dehydrogenation of oxygen-containing cyclohexane derivatives is one of the basic petrochemical processes. It can be exemplified by dehydrogenation of cyclohexanol into cyclohexanone which is a mass-scale product of caprolactam manufacture, or dehydragenation of cyclohexanol to phenol which, in turn, is the most important chemical product, or dehydrogenation of cyclohexanediol-1,2 to pyrocatechol—an intermediate for the manufacture of highly-efficient additives to petrochemicals and polymers. All these processes are carried out in the presence of heterogeneous catalysts—usually metals of Group VIII of the periodic system, or copper supported on inert carriers.

BACKGROUND OF THE INVENTION

Known in the art is a catalyst for dehydrogenation of oxygen-containing cyclohexane derivatives containing, as the active component, nickel as well as promotors—copper, chromium and sodium sulphate supported on an inert carrier (cf. U.S. Pat. No. 2,640,084 Cl. 260-621, 1953). However, this prior art catalyst possesses an insufficient productivity in dehydrogenation of mono-oxygen-containing derivatives of cyclohexane, e.g. cyclohexanol or cyclohexanone: at the temperature of 350° C. the desired product—phenol—is formed at a rate of not more than 0.15 kg per 1 liter of the catalyst per hour.

Furthermore, in the dehydrogenation of cyclohexane derivatives containing more than one oxygen atom per molecule a side process of dehydration intensively proceeds in the presence of this catalyst. as a result, selectivity for the desired dihydric phenols, for example in dehydrogenation of cyclohexanediol-1,2 to pyrocatechol is very low and does not exceed 15-20%.

Also known in the art is a catalyst for dehydrogenation of oxygen-containing derivatives of the cyclohexane series which corresponds to the following general formula:

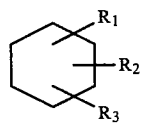

wherein $R_1$ is hydrogen or a $C_1$–$C_4$ alkyl, $R_2$ and $R_3$ are radicals having the same or different meanings: —OH, —H, =O, provided that $R_2$ and $R_3$ are not simultaneously hydrogen, $R_1$, $R_2$ and $R_3$ are attached to different carbon atoms of the cycle, into corresponding cyclic ketones and/or phenols which contains, as the active ingredient, a metal of Group VIII of the periodic system, such as nickel, as well as a promotor such as tin, and an inert carrier—silica. The atomic ratio between the metal of Group VIII and tin in this catalyst is varied within the range of from 1.7:1 to 15:1 respectively. Proportions of these components in the catalyst are selected within the following limits, percent by weight:

| | |
|---|---|
| metal of Group VIII of the periodic system | 2 to 20 |
| tin | 2 to 30 |
| inert carrier | the balance |

(cf. H. E. Swift, J. E. Bozik, J. Catal., v.12, p.5/1968/; U.S. Pat. No. 3,580,970 Cl. 260–621H, 1971).

This prior art catalyst, however, has a disadvantage residing in its low productivity for ketones and phenols and an insufficient stability. Thus, in dehydrogenation of cyclohexanone the productivity (relative to phenol) of the nickel-tin catalyst of an optimal composition (atomic ratio of nickel:tin is 2.5:1) deposited on silica is 1.3 kg/l.hr at the temperature of 375° C., while after 8 hours it is reduced to 1.0 kg/l.hr and even below (see FIG. 4 of the cited U.S. Patent). Similar results have been pointed to in publication by M. Masai et al. (J. Catal., v.38, p.128, 1975): upon dehydrogenation of cyclohexanone on a nickel-tin catalyst (nickel:tin=2.5:1) at the temperature of 400° C. the initial productivity for phenol is 1.0 and 8 hours after only 0.6 kg/l.hr.

Selectivity of the prior art catalyst in dehydrogenation of monofunctional oxygen-containing derivatives of cyclohexane to phenol is high enough (up to 98%), though its selectivity for ketones is not high; thus, in dehydrogenation of cyclohexanol into cyclohexanone it does not exceed 50% (cf. op.cit. paper by H. E. Swist and J. E. Bozik). Especially low is selectivity of the prior art catalyst in dehydrogenation of polyfunctional oxygen-containing derivatives of the cyclohexane series into corresponding polyfunctional phenols. Thus, in dehydrogenation of cyclohexanediol-1.2 into pyrocatechol at the temperature of 330° C. and below the selectivity for the desired product does not exceed 30%, whereas at 330° C. side processes intensively occur, thus causing an accelerated deactivation of the catalyst.

Known is a process for dehydrogenation of oxygen-containing derivatives of the cyclohexane series of the abovegiven general formula feedstock) into corresponding cyclic ketones and/or phenols which comprises contacting oxygen-containing derivatives of the cyclohexane series with a nickel-tin catalyst of the above-mentioned composition at a temperature within the range of from 375° to 400° C. in the presence of hydrogen employed in the 6-fold molar excess relative to the feedstock (cf. H. E. Swift, J. E. Bozik, J. Catal., v.12, p.5/1968/; U.S. Pat. No. 3,580,970 Cl. 260–621H, 1971).

The above-discussed disadvantages of the prior art nickel-tin catalyst entail disadvantages of the process for dehydrogenation of oxygen-containing compounds of the cyclohexane series making use of this prior art catalyst. Thus, the use of a low-efficient catalyst causes a low productivity of the entire dehydrogenation process, while an insufficient stability of the catalyst results in impaired parameters of the process on the whole (the conversion of the starting materials, selectivity and yield of the desired products) with time and necessitates temporary shutdown of the dehydrogenation line for regeneration of the catalyst.

To improve stability of the catalyst, in the prior art process the catalyst composition additionally incorporates expensive platinum, chromium and sodium sulphate; this, however, substantially lowers productivity of the catalyst and the process of dehydrogenation to about 0.2 kg/l.hr.

SUMMARY OF THE INVENTION

It is an object of the present invention to provide a catalyst for dehydrogenation of oxygen-containing derivatives of the cyclohexane series of the above-given general formula into corresponding cyclic ketones and/or phenols which would feature high characteristics of productivity, selectivity and stability.

It is another object of the present invention to provide a process for dehydrogenation of oxygen-containing derivatives of the cyclohexane series which would make it possible to obtain corresponding cyclic ketones and/or phenols in high yield and with an increased productivity.

These and other objects of the present invention are accomplished by a catalyst for dehydrogenation of oxygen-containing derivatives of the cyclohexane series having the following general formula:

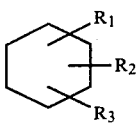

wherein $R_1$ is hydrogen or a $C_1-C_4$ alkyl, $R_2$ and $R_3$ are radicals having the same or different meanings: —H, —OH, =O, provided that $R_2$ and $R_3$ are not simultaneously hydrogen, $R_1$, $R_2$ and $R_3$ are attached to different carbon atoms of the cycle, into corresponding cyclic ketones and/or phenols which comprises an active component—nickel, a promotor—germanium and/or lead and an inert carrier—silica, kieselguhr, silicon carbide or magnesia; the component proportions in the catalyst composition are as follows, percent by weight:

| nickel | 15 to 55 |
|---|---|
| promotor | 0.2 to 8.0 |
| inert carrier | 84.8 to 37.0 | and the atomic ratio between nickel and the promotor is from 15:1 to 410:1 respectively.

The highest productivity is manifested by a catalyst containing 15 to 55% by weight of nickel supported on the above-specified inert carrier. At a content of nickel below 15% the catalyst productivity is sharply reduced; a content of nickel above 55% is inadvisable, since it does not result in improvement of useful properties of the catalyst.

For the above-specified content of nickel the improvement of selectivity and stability of the catalyst operation is attained due to the incorporation of a promotor in an amount ranging from 0.2 to 8.0% by weight of the catalyst; the atomic ratio between nickel and the promotor should be within the range of from 15:1 to 410:1 respectively. At a content of the promotor below 0.2% by weight and at the atomic ratio of nickel:promotor above 410:1 the catalyst has a slow selectivity and decreased stability under the conditions of dehydrogenation of oxygen-containing derivatives of the cyclohexane series: side process of dehydration and condensation occur so that the catalyst is rapidly coking and deactivating. At a content of the promotor above 8.0% by weight and atomic ratio of nickel:promotor below 15:1 the catalyst productivity is sharply lowered, especially in the reaction of the formation of phenols.

In order to increase selectivity and productivity of the catalyst for dehydrogenation of oxygen-containing derivatives of the cyclohexane series at elevated temperatures (above 300° C.), it is advisable to introduce, into the catalyst composition, a salt of an alkali metal and a mineral acid in an amount of from 0.01 to 1.0% by weight. Cations of such salts can be exemplified by lithium, potassium, sodium, calcium, barium; anions - chloride, sulphate, fluoride, sulphide, phosphate and the like. The lower limit of the content of said salt corresponds to the minimal concentration of the additive in the catalyst ensuring the noticeable effect of increasing its selectivity and productivity. At a content of the alkali metal and mineral acid salt above 1.0% by weight the catalyst productivity is sharply reduced.

The object of the present invention is also accomplished by a process for dehydrogenation of oxygen-containing derivatives of the cyclohexane series of the above-given general formula into corresponding cyclic ketones and/or phenols with the use of the catalyst according to the present invention. In the process of this invention oxygen-containing derivatives of cyclohexane are contacted with the catalyst in the presence of a diluent—an inert gas, aliphatic $C_1-C_4$ hydrocarbons, nitrogen, carbon dioxide, steam, aliphatic $C_1-C_3$ alcohols or different combinations thereof at a temperature within the range of from 160° to 340° C. and a partial pressure of the oxygen-containing derivatives of the cyclohexane series ranging from 0.003 to 0.1 atm. Feed rates of said oxygen-containing derivatives of the cyclohexane series and the diluent are equal to 0.5-5.0 kg/l.hr and 1-53 m³/l.hr respectively.

The function of the diluent resides in increasing of the equilibrium yield of the desired dehydrogenation products. Since this process is reversible and occurs with increasing number of molecules, the dilution of the starting oxygen-containing derivative of the cyclohexane series to partial pressures within the range of from 0.003 to 0.1 atm improves the yield of the desired product.

To ensure a high productivity, in the process for dehydrogenation according to the present invention it is necessary to supply the feedstock at a high rate of from 0.5 to 5.0 kg/l.hr. It is also possible to carry out the process according to the present invention beyond the above-specified range of the feedstock rates; however, at a feed rate below 0.5 kg/l.hr a decreased catalyst productivity is observed, while at a feed rate above 5.0 kg/l.hr the conversion of oxygen-containing derivatives of the cyclohexane series does not exceed 70% which hinders isolation of the desired products from the catalysate. In compliance with the above-specified feed rates and requirements of the feedstock dilution, the selected range of the diluent feed rate is defined as of from 1 to 53 m³/l.hr.

The dehydrogenation process according to the present invention can be effected at temperatures both below 160° and above 340° C. However, at temperatures below 160° C. the reaction mixture after contacting consists by more than 80% of the unreacted feedstock which hinders isolation of the desired ketones and/or phenols. In the case where the process of dehydrogenation is conducted at a temperature above 340° C., side processes of dehydration and resinification start to proceed more intensively which results in the formation of condensation products deactivating the catalyst.

Therefore, it has been quite unexpectedly found that the catalyst according to the present invention containing minor additives of a promotor to nickel (0.2–8.0% by weight) and having an atomic ratio of nickel:promotor of 15:1 and above possesses a high productivity (up to 3.8 kg/l.hr), selectivity (up to 99%) and a high-stability in the process of dehydrogenation of oxygen-containing dervatives of the cyclohexane series. These characteristics remain unchanged during a long-time operation of the catalyst for at least 400 hours. The catalyst according to the present invention makes it possible to carry out dehydrogenation of oxygen-containing derivatives of the cyclohexane series into corresponding ketones (at temperatures of 200° C. and below), phenols (at temperatures of 240° C. and above) or mixtures thereof.

It should be noted that the catalyst according to the present invention, in contrast to the prior art nickel-containing catalysts, makes it possible to effect dehydrogenation of oxygen-containing derivatives of the cyclohexane series into corresponding polyfunctional phenols, e.g. cyclohexanediol-1,2 into pyrocatechol, at a high selectivity (up to 94%). Furthermore, the catalyst according to the present invention, in contrast to the prior art nickel-containing catalysts, makes it possible to steadily carry out dehydrogenation of oxygen-containing organic compounds in the atmosphere of water vapours, without poisoning with impurities of sulphur compounds which may be present in the reaction mixture.

An advantage of the catalyst according to the present invention resides in its sufficiently simple composition incorporating inexpensive and readily-available metals such as nickel, germanium and/or lead. The catalyst according to the present invention is prepared by conventional procedures using standard equipment.

The use of the catalyst according to the present invention has made it possible to carry out a high-efficiency process for dehydrogenation of oxygen-containing derivatives of the cyclohexane series into corresponding ketones and/or phenols: productivity for ketones, mono- and polyhydric phenols is equal to 3.4–3.8 kg/l.hr. Selectivity for ketones, phenol and polyhydric phenols is equal to 97–99% at a substantially total conversion of the starting reagents, thus considerably facilitating the problem of isolation of the desired products from the reaction mixture and protection of the environment.

It should be also noted that the improvement of characteristics of productivity, yield and selectivity of the desired products is achieved in the process of this invention together with a considerable reduction of the dehydrogenation temperature to 160°–340° C. instead of 375°–400° C. in the prior art process. This results in a lowered energy consumption and makes the dehydrogenation process of the present invention even more economically efficient.

The process for dehydrogenation of oxygen-containing derivatives of the cyclohexane series is rather simple and can be effected on standard equipment.

DETAILED DESCRIPTION OF THE INVENTION

The catalyst according to the present invention is prepared following a conventional procedure by way of impregnation of powder-like inert carriers such as silica, kieselguhr, silicon carbide, magnesia with nickel salts and salts of a promotor (germanium and/or lead) in a medium of water, organic polar solvents such as alcohols, amines, dialkylsulphates, dialkylsulphoxides or different combinations thereof. In the case of using a mixed promotor, its components (germanium, lead) can be employed in any proportions.

As the inert carrier use can be made of any out of the above-mentioned carriers having sufficiently developed specific area, for example of from 2 to 250 $m^2/g$ with a pore size of from 10 to 1,000 Å.

As the salts of nickel and promotor (germanium and/or lead) use can be made of any salts of organic and inorganic acids decomposing at a temperature of not more than 400° C. For example, use can be made of chlorides, nitrates and sulphates of the above-mentioned metals, their complexes with ammonia, as well as salts of formic acid, acetic acid, propionic acid and other acids.

After impregnation of the inert carrier with solutions of the above-mentioned salts of nickel and promotor in the solvents specified hereinabove at a temperature within the range of from 10° to 100° C. under stirring for 12 to 70 hours, the mixture is dried for 2–3 hours at a temperature of from 80° to 120° C. and then calcined at a temperature ranging from 400° to 500° C. for 3 to 5 hours. The resulting powder-like catalyst is shaped in tablets with a size of from 1 to 3 mm, charged into a tubular flow-type reactor and reduced with a hydrogen-containing gas at a gradual increase in of temperature to 400°–450° C. and maintaining at this temperature for a period of from 2 to 6 hours. Pressure of hydrogen is 0.2 to 20 atm.

Another embodiment of the procedure for the preparation of the catalyst comprises application, onto a shaped inert carrier, of volatile compounds of nickel and promoter by adsorption of these compounds on the inert carrier from the gas phase. As volatile nickel compounds use can be made, for example, of nickel carbonyl or $\pi$-allyl complexes of nickel. As volatile compounds of germanium and lead use is made of their organic compounds such as tetramethylgermanium, tetrapropylgermanium, tetramethyllead and the like.

In the case of use of organic or carbonyl compounds of nickel and organic compounds of the promoter in the preparation of the catalyst there is no need in the operation of calcination of nickel and promoter compounds on the carrier in the air atmosphere.

In doing so, the final catalyst can be obtained by reduction of carbonyl or organic compounds of nickel and organic compounds of the promotor with hydrogen at an elevated temperature, directly after the stage of adsorption of these compounds on the carrier. The operation of reduction of nickel and promotor compounds is effected in a stream of hydrogen at a temperature within the range of from 200° to 450° C. under a pressure of hydrogen of from 0.2 to 20 atm.

The final reduced catalyst is purged with an inert gas, nitrogen or carbon dioxide at the reduction temperature for 15–30 minutes while lowering temperature to 160°–340° C. and catalytic dehydrogenation of oxygen-containing derivatives of the cyclohexane series (feedstock) is effected thereon.

As the above-specified oxygen-containing derivatives of the cyclohexane series of the above-given general formula use can be made of, for example, cyclohexanol, cyclohexanone, alkylsubstituted cyclohexanol and cyclohexanone such as methyl-, butyl- and tert.butylcyclohexanol, cyclohexanediol-1,2; cyclohexanediol-1,3; cyclohexanediol-1,4; cyclohexanetriols, 2-hydroxycyclohexanone, cyclohexanedione-1,2; cyclohexanedione-1,4; alkylsubstituted cyclohexanediols such as tert. butylcyclohexanediol-1,2; ethylcyclohexanediol-1,2 and the like.

The process for dehydrogenation of oxygen-containing derivatives of the cyclohexane series resides in that into a tubular flow-type reactor provided with an evaporator positioned before the catalyst bed there are fed, after reduction of the catalyst, vapours of the feedstock diluted to a pressure of from 0.003 to 0.1 atm with an inert gas, $C_1$–$C_4$ aliphatic hydrocarbons, nitrogen, carbon dioxide, steam, $C_1$–$C_3$ aliphatic alcohols or different combinations thereof, e.g. a mixture of steam and carbon dioxide, a mixture of steam and methane, a mixture of nitrogen and $C_1$–$C_4$ aliphatic hydrocarbons. The dehydrogenation temperature is varied within the range of from 160° to 340° C. Dehydrogenation can be carried out under any pressure, though it is most preferable to use pressure approaching the atmospheric.

In the use of compounds soluble in water or above-specified aliphatic alcohols as the starting feedstock, it is convenient to carry out the supply of these compounds into the reactor in the form of solutions in said solvents. The latter, after evaporation in the reactor (evaporator) act as diluents.

In the case where as the starting stock use is made of gaseous diluents, compounds are employed which comprise liquids or solid compounds under normal conditions which should be preliminary melted, for example cyclohexanediols and derivatives thereof. In this case the supply of the feestock into the reactor is effected by bubbling a gaseous diluent through a liquid or molten feedstock, or by separately supplying the feedstock as fine liquid drops and the diluent in the gaseous state.

The reaction mixture effluent from the reactor after contacting with the catalyst is entrained in traps at a temperature within the range of from (−78)° to (+20)° C. The resulting catalysate is homogenized by the addition of ethanol or another solvent and the solution is chromatographically (GLC) analyzed with the use of a flame-ionization detector. The chromatographic column contains 10% of Lukooil DF supported on Cromaton NAW; the column temperature is 100° to 160° C., helium supply rate is 45 ml/min. Furthermore, for the purpose of physico-chemical analysis of the catalysate, organic compounds are extracted fron water with carbon tetrachloride, butanol, butylacetate and the like. Pure compounds are recovered by distillation of the extracts after evaporation of the solvent. The structure of the desired products is justified by means of spectral characteristics (UV-spectra), qualitative reactions on individual functional groups, as well as ultimate analysis.

For a better understanding of the present invention some specific examples illustrating its embodiments are given hereinbelow. Unless otherwise specified, the time of the catalyst run in the Examples is 6 hours.

EXAMPLE 1

A catalyst is prepared which has the following composition, percent by weight:

| nickel | 55 |
|---|---|
| lead | 8 |
| kieselguhr | 37. |

The atomic ratio of nickel:lead is 24.3:1.

To 10.0 g of kieselguhr (powder with a particle size of 10–50 μm and specific surface area of 90 m$^2$/g) there are poured 30 ml of an aqueous solution of nickel and lead nitrates containing 14.9 g of nickel and 2.2 g of lead, stirred for 3 hours at the temperature of 25° C., maintained for 12 hours and water is evaporated to produce a paste. The paste is dried at the temperature of 110° C. for two hours in the air, shaped to tablets with the diameter of 3 mm and thickness of 1 mm and calcined at the temperature of 400° C. for 3 hours in a stream of a humid (1% humidity) air. After cooling the catalyst is obtained in its oxidized form.

Into the reactor there are charged 5 ml of the catalyst in the oxidized form. The reactor comprises a quartz tube with the diameter of 13 mm, length of 400 mm having a porous partition in the middle to accommodate the catalyst bed. Over the catalyst there are charged 20 ml of crushed quartz to improve conditions for evaporation of the starting feedstock. The oxidized nickel-lead catalyst is reduced in a stream of hydrogen diluted with nitrogen (1:5 by volume) at a gradual elevation of temperature from 20° to 400° C. (2 hours) and by means of pure hydrogen (10 l/hr) at the temperature of 400° C. for 3 hours. Under these conditions, according to the data of X-ray analysis and ultimate analysis by the method of atomic-absorption spectroscopy, there occurs a complete reduction of compounds of nickel and lead to metals and the reduced catalyst has the above-specified composition.

The reduced catalyst is purged for 15 minutes with nitrogen at the temperature of 400° C., temperature is lowered to 160° C. in a stream of nitrogen and the catalytic dehydrogenation of cyclohexanol is carried out.

Into a reactor preheated to the temperature of 160° C. from a dropping funnel cyclohexanol is added at the rate of 3.5 kg/l.hr and steam at the rate of 6.05 m$^3$/l.hr. The partial pressure of cyclohexanol is 0.1 atm. The reaction products after contacting with the catalyst are entrained in two traps at the temperature of 20° and −78° C. respectively. At the interval of 30 minutes the catalysate from the traps is homogenized by adding 50% of ethanol thereto and chromatographic analysis is carried out at the column temperature of 100° C. According to the data of the chromatographic analysis, the catalysate consists of the following components, percent by weight: 65.8—cyclohexanone, 4.2—cyclohexene and 30—cyclohexanol. The conversion of the feedstock is 70%, selectivity and productivity for cyclohexanone is 94% by weight and 2.3 kg/l.hr respectively. These parameters remain unchanged during non-stop operation of the catalyst for 240 hours.

EXAMPLE 2

A catalyst is prepared which has the following composition, percent by weight:

| | |
|---|---|
| nickel | 23.3 |
| lead | 0.2 |
| kieselguhr | 76.5. |

The atomic ratio of nickel:lead is 410:1.

To 10.0 g of kieselguhr (powder with a particle size of from 10 to 50 μm and specific surface area of 90 m$^2$/g) there are added 25 ml of an aqueous solution of nickel nitrate containing 3.1 g of nickel, stirred for 10 hours at the temperature of 30° C., dried at the temperature of 90° C. to give a paste. The resulting paste is added with 20 ml of a solution of lead acetate (II) in dimethylformamide containing 0.03 g of lead. The mixture is stirred for 2 hours at 20° C., mainained for 20 hours and the solvent is evaporated at 80° C. in vacuum for 3 hours. The resulting powder is shaped to tablets (3×1 mm) and calcined at 450° C. for 3 hours in a current of humid (1%) air to give the catalyst in the oxidized form.

Into a reactor there are charged 5 ml of the catalyst in the oxidized form and reduction is carried out as in Example 1. The reduced catalyst, according to analytical data, has the composition specified hereinabove.

The reduced catalyst in a stream of nitrogen is cooled to the temperature of 220° C. and the catalytic dehydrogenation of cyclohexanol is conducted following the procedure described in the foregoing Example 1. The feedstock rate is 3.5 kg/l.hr, that of nitrogen—6.05 m$^3$/l.hr, the partial pressure of the feedstock is 0.1 atm. The reaction mixture is condensed following the procedure of Example 1 and chromatographic analysis of the homogenized catalysate is conducted at the column temperature of 100° C. According to the data of chromatographic analysis, the catalysate consists of the following components, percent by weight: cyclohexanone 19.6, phenol 78.4 and cyclohexanol 2. The conversion of cyclohexanol is 98%, selectivity for phenol and cyclohexanone is 80 and 20% respectively, productivity for phenol—2.74 kg/l.hr.

EXAMPLE 3

A catalyst is prepared which has the following composition, percent by weight:

| | |
|---|---|
| nickel | 15 |
| lead | 0.2 |
| silica | 84.8. |

The atomic ratio of nickel:lead is 265:1.

To 20 g of silica (powder with a particle size of from 10 to 50 μm and specific surface area of 25 m$^2$/g) there are added 50 ml of an aqueous solution of nickel chloride containing 3.6 g of nickel, stirred for 2 hours at the temperature of 20° C., the mixture is kept for 20 hours at the temperature of 50° C. and water is evaporated at 90° C. to give a paste. The resulting paste is added with 40 ml of a solution of lead acetate (II) in dimethylsulphoxide containing 0.048 g of lead. The mixture is stirred for 2 hours, kept for 6 hours at 25° C. and water is evaporated. The resulting paste is dried at the temperature of 100° C. in the air for two hours, shaped to tablets (3×1 mm) and calcined at 400° C. for 5 hours in a stream of humid (1% humidity) air to give a catalyst in the oxidized form.

Into a reactor there are charged 3 ml of the catalyst in the oxidized form and reduction is carried out as described in Example 1 hereinbefore. The reduced catalyst has, according to the data of analyses, the composition specified hereinabove.

The reduced catalyst in a stream of helium is cooled to 340° C. and catalytical dehydrogenation of cyclohexanone is carried out. The feed rates of the liquid feedstock and the diluent (helium) are 2.0 kg/l.hr and 8.5 m$^3$/l.hr respectively; the partial pressure of the feedstock is 0.05 atm. The reaction mixture is condensed and chromatographic analysis of the catalysate is carried out at the column temperature of 100° C. According to the chromatographic analysis data the catalysate consists of the following components, percent by weight: phenol—98.0, 2-/1-cyclohexenyl/-cyclohexanone—2.0%. The conversion of cyclohexanone is 100%, selectivity for phenol is 98%, productivity for phenol is 1.96 kg/l.hr.

EXAMPLE 4

A catalyst is prepared which has the following composition, percent by weight:

| | |
|---|---|
| nickel | 30 |
| lead | 0.9 |
| magnesia | 69 |
| dipotassium hydrogen phosphate | 0.1. |

The atomic ratio between nickel and lead is 118:1.

To 20 g of magnesia (powder with a particle size of 10 to 50 μm and specific surface area of 40 m$^2$/g) there are added 40 ml of an aqueous solution containing 8.7 g of nickel and 0.27 g of lead as acetate and 0.03 g of K$_2$HPO$_4$. The mixture is stirred for two hours, maintained for 24 hours at the temperature of 20° C., then water is evaporated at 90° C. to give a paste. The paste is dried at 110° C. in the air for 3 hours, shaped to tablets (3×1 mm) and calcined at 450° C. in a stream of humid air to give the catalyst in its oxidized form.

Into a reactor there are charged 3 ml of the catalyst in the oxidized form and reduction is conducted as in Example 1 at the temperature of 450° C. for 3 hours. The reduced catalyst has, according to the data of analyses, the composition specified hereinabove.

The reduced catalyst in a stream of methane fraction (methane content about 95% by volume, the balance—higher C$_2$-C$_4$ homologues) is cooled to 300° C. and catalytic dehydrogenation of cyclohexanone is carried out. The feed rates of the liquid feedstock and the diluent (methane fraction) is 0.8 kg/l.hr and 53 m$^3$/l.hr respectively; the partial pressure of the feedstock is 0.003 atm. The reaction mixture is condensed in two traps at the temperature of 20° and −78° C. respectively and chromatographic analysis of the catalysate is carried out at the column temperature of 100° C. According to data of chromatographic analysis, the catalysate consists of the following components, percent by weight: phenol—98, cyclohexanone—2. The degree of conversion of cyclohexanone is 98%, selectivity and productivity for phenol is 100% and 0.78 kg/l.hr respectively.

EXAMPLE 5

A catalyst is prepared which has the following composition, percent by weight:

| | |
|---|---|
| nickel | 15 |

| | |
|---|---|
| lead | 3.5 |
| silicon carbide | 81.5 |

The atomic ratio between nickel and lead is 15:1.

To 20 g of silicon carbide (powder with a particle size of from 10 to 50 μm and specific area of 4 m²/g) there are added 40 ml of an aqueous solution containing 3.7 g of nickel and 0.86 g of lead in the form of their acetates. The mixture is treated, moulded and reduced following the procedure described in the foregoing Example 4 to give the catalyst having the composition specified hereinabove.

The reduced catalyst in a stream of carbon dioxide is cooled to 200° C. and catalytical dehydrogenation of cyclohexanediol-1.2 is carried out. The feed rates of the preliminarily melted feedback, steam and carbon dioxide is 1.0 kg/l.hr, 2.0 and 2.0 m³/l.hr respectively; the partial pressure of cyclohexanediol-1.2 is equal to 0.05 atm. The reaction mixture is condensed in two traps at the temperature of −20° and 20° C. respectively. The liquid catalysate is homogenized by adding 50 vol.% of ethanol thereto and chromatographic analysis is carried out at a temperature of the column of from 100° to 155° C. (programmed heating). According to the data of chromatographic analysis, the catalysate consists of the following components, percent by weight: 2-hydroxycyclohexanone—50, pyrocatechol—30, cyclohexanediol-1,2—20. The presence of 2-hydroxycyclohexanone in the catalyst is proved, after isolation thereof by recrystallization from an aqueous solution of ethanol (70 vol.%), by the methods of IR- and UV-spectroscopy. IR-spectrum: absorption bands in the range of 3,470 and 1,720 cm$^{-1}$; UV-spectrum-absorption in the region of 263 nm. Furthermore, 2-hydroxycyclohexanone recovered from the catalysate gives a characteristic (for the acyloine grouping—CO—CH(OH)—) reaction with bismuth (III) ion with precipitation of metallic bismuth. The presence of pyrocatechol in the catalysate is demonstrated by the formation of a white precipitate of a lead salt of pyrocatechol upon the addition of an alcoholic solution of lead acetate (II) to the catalysate.

The conversion of cyclohexanediol-1,2 is 80%, selectivity and productivity for 2-hydroxycyclohexanone is 62.5% and 0.5 kg/l.hr respectively.

EXAMPLE 6

A catalyst is prepared having the following composition, percent by weight:

| | |
|---|---|
| nickel | 30 |
| germanium | 1 |
| silica | 69. |

The atomic ratio between nickel and germanium is 37:1.

Into a stainless steel tubular reactor there are charged 3 g of silica (powder with a particle size of from 0.5 to 2 mm and specific surface area of 200 m²/g) and the reactor is heated to the temperature of 300° C. A stream of vapours of nickel carbonyl produced by treating a foil (0.1 mm) of nickel weighing 1.5 g with carbon monoxide at the temperature of 130° C. is passed through the bed of silica. After substantially total consumption of the nickel foil (which takes about 5 to 6 hours), the pipings and reactor are purged with nitrogen for 10 minutes. Then at the temperature of 300° C. into the reactor tetramethylgermanium is fed by bubbling nitrogen into a solution of 0.08 g of tetramethylgermanium in dry benzene for 2 hours. On completion of admission of tetramethylgermanium, hydrogen is admitted into the reactor to the pressure of 10 atm and under this pressure and at the temperature of 300° C. silica with the deposited thereon compounds of silicon and germanium is treated with hydrogen for 3 hours. According to the data of electronographic and atom-absorption analyses, such treatment results in the production of a catalyst which contains nickel and germanium as metals. The catalyst has the composition specified hereinabove.

The reduced catalyst in a stream of nitrogen is cooled to the temperature of 180° C. and catalytic dehydrogenation of cyclohexanediol-1,2 is carried out. The starting feedstock is supplied into the reactor as a melt at the rate of 0.81 kg/l.hr; the feed rate of nitrogen is 1.4 m³/l.hr, partial pressure of the feedstock is equal to 0.1 atm.

The reaction mixture is condensed in two traps at the temperature of −20° and +20° C. respectively, dissolved in ethanol and chromatographically analyzed at the column temperature of 150° C. According to the data of chromatographic analysis, the catalyzate consists of the following components, percent by weight: 2-hydroxycyclohexanone—80, cyclohexanediol-1,2—20.

The conversion of cyclohexanediol-1,2 is 80%, selectivity for 2-hydroxycyclohexanone—100%, productivity—0.64 kg/l.hr.

EXAMPLE 7

Following the procedure described in Example 6 hereinabove, a catalyst is prepared which has the following composition, percent by weight:

| | |
|---|---|
| nickel | 31 |
| germanium | 0.5 |
| lead | 1.6 |
| silica | 66.9. |

The atomic ratio of nickel to (germanium+lead) is 35.4:1.

To prepare the catalyst of the above-specified composition, per 3 g of silica there are used 1.38 g of nickel foil, 42 mg of tetramethylgermanium and 115 mg of tetraethyllead. The organic compounds of germanium and lead are employed as a solution in dry benzene. The carrier containing nickel and organic compounds of germanium and lead is treated with hydrogen as described in Example 6 to give the catalyst of the composition indicated hereinabove.

The reduced catalyst in the stream of nitrogen is cooled to 250° C. and catalytic dehydrogenation of 2-hydroxycyclohexanone is carried out, the product being supplied in the form of a solution (5 mol.%) in ethanol. The feed rate of 2-hydroxycyclohexanone is equal to 1.16 kg/l.hr, partial pressure of the starting feedstock is 0.05 atm. Vapours of ethanol serve as the diluent. The reaction mixture is condensed in two traps at the temperature of −20° and 20° C. respectively to give an ethanolic solution of the catalysate. The chromatographic analysis of the catalysate is conducted at a temperature within the range of from 110° to 150° C. According to the data of this analysis, the catalysate consists of the following components, percent by weight: pyrocatechol—94, phenol—6. The conversion of 2-hydroxycyclohexanone is 100%, selectivity and productivity for pyrocatechol are 94% and 1.09 kg/l.hr respectively.

EXAMPLE 8

Following the procedure described in Example 4 hereinbefore, a catalyst of the following composition is prepared, percent by weight:

| | |
|---|---|
| nickel | 55 |
| lead | 5.4 |
| magnesia | 38.6 |
| sodium sulphate | 1. |

The atomic ratio between nickel and lead is 36:1.

The difference resides in that the impregnation aqueous solution (volume of 60 ml) contains 28.6 g of nickel and 2.8 g of lead in the form of their respective acetates and 0.52 g of sodium sulphate.

The catalyst is treated, shaped and reduced as described in Example 4. The reduced catalyst (3 ml) is charged into the reactor in a stream of nitrogen and catalytic dehydrogenation of cyclohexanediol-1,4 is carried out at the temperature of 300° C. The feedstock is supplied into the reactor as a 10% aqueous solution at the rate of 3.5 kg/l.hr. Furthermore, nitrogen is admitted into the reactor at the rate of 27.3 m$^3$/l.hr. The partial pressure of the feedstock is 0.01 atm.

The reaction mixture is condensed in two traps at the temperature of −20° and 20° C. respectively. The contents of these traps are subjected to chromatographic analysis at a temperature within the range of from 110° to 150° C. Based on the data of this analysis, the catalysate consists of the following components, percent by weight: hydroquinone—86, phenol—14. The conversion of cyclohexanediol-1;4 is equal to 100%, selectivity and productivity for hydroquinone are 86% and 3.01 kg/l.hr respectively.

EXAMPLE 9

A catalyst is prepared which has the following composition, percent by weight:

| | |
|---|---|
| nickel | 41 |
| lead | 4.5 |
| kieselguhr | 54.49 |
| sodium sulphide | 0.01. |

The atomic ratio of nickel:lead is 32:1.

To 10 g of kieselguhr (powder with a particle size of from 10 to 50 μm and specific surface area of 90 m$^2$/g) there are poured 35 ml of an aqueous solution containing 7.6 g of nickel and 0.83 g of lead in the form of their respective chlorides, as well as 2 mg of sodium sulphide. The mixture is treated, shaped and reduced as described in Example 1 to give the catalyst the above-indicated composition.

In a stream of helium into the reactor there are charged 3 ml of the reduced catalyst and catalytic dehydrogenation of 4-ethylcyclohexanediol-1,2 is carried out at the temperature of 320° C. The starting feedstock is supplied into the reactor as a 1 mol.% solution in methanol at the rate of 2.32 kg/l.hr, the partial pressure of the feedstock is 0.01 atm.

The reaction mixture is condensed and analyzed as described in Example 8 hereinbefore. According to the data of chromatographic analysis the catalysate consists of the following components, percent by weight: 4-ethylpyrocatechol—94 and phenol—6. The conversion of 4-ethylcyclohexanediol-1,2 is 100%, selectivity and productivity for 4-ethylpyrocatechol are 94% and 2.18 kg/l.hr respectively.

EXAMPLE 10

Following the procedure of Example 1, a catalyst is prepared which has the following composition, percent by weight:

| | |
|---|---|
| nickel | 50 |
| lead | 7 |
| kieselguhr | 42.5 |
| lithium chloride | 0.5. |

The atomic ratio of nickel:lead is 25:1.

The difference resides in that the impregnating aqueous solution (volume of 35 ml) contains 11.8 g of nickel and 1.7 g of lead in the form of their nitrates, as well as 0.12 g of lithium chloride. The mixture is treated, shaped and reduced as described in Example 1 to give the catalyst of the above-specified composition.

In a stream of carbon dioxide into the reactor there are charged 3 ml of the reduced catalyst and catalytic dehydrogenation of cyclohexanediol-1,3 is conducted at the temperature of 340° C. The starting feedstock is supplied into the reactor in the form of a 6 mol.% aqueous solution at the rate of 2.32 kg/l.hr, the partial pressure of the feedstock is 0.06 atm. Water vapours serve as the diluent. The reaction mixture is condensed in two traps at the temperature of −20° and 20° C. The contents of the traps are subjected to chromatographic analysis at a temperature of from 110° to 150° C. Based on the data of this chromatographic analysis, the catalysate consists of the following components, percent by weight: resorcinol—90 and phenol —10. The conversion of cyclohexanediol-1,3 is 100% selectivity and productivity for resorcinol are 90% and 2.09 kg/l.hr respectively.

EXAMPLE 11

The catalyst prepared in Example 10 is used. The reduced catalyst (3 ml) is heated in a stream of nitrogen to the temperature of 330° C. and catalytic dehydrogenation of cyclohexanediol-1,2 is carried out. The feedstock is supplied into the reactor as a 20% aqueous solution at the rate of 5.0 kg/l.hr; the feed rate of nitrogen is 22.4 m$^3$/l.hr. The partial pressure of the feedstock is 0.02 atm. The catalysate is analyzed as described in Example 10. According to the data of the analysis, the catalysate consists of the following components, percent by weight: pyrocatechol—72, 2-hydroxycyclohexanone—11, phenol—7 and cyclohexanediol-1,2—10. The conversion of cyclohexanediol-1,2 is 90%, selectivity and productivity for pyrocatechol are 80% and 3.6 kg/l.hr respectively. Pyrocatechol is readily isolated from the catalysate comprising an aqueous solution or organic compounds by extraction with carbon tetrachloride, followed by distilling-off phenol and the solvent. The resulting pyrocatechol has purity over 99.5%, its melting point is 105° C.

EXAMPLE 12

Use is made of the catalyst prepared as described in Example 7 hereinbefore. The reduced catalyst (3 ml) is heated in a stream of nitrogen to the temperature of 260°

C. and catalytic dehydrogenation of 4-tert.butylcyclohexanediol-1,2 is carried out. The feed is supplied into the reactor as a solution (5 mol.%) in propanol at the rate of 1.16 kg/l.hr. The partial pressure of the feedstock is 0.05 atm.

The reaction mixture is condensed in two traps at the temperature of −20° and 20° C. and chromatographically analyzed at a temperature of from 110° to 160° C. According to the data of the analysis the catalysate consists of the following components, percent by weight: 4-tert.butyl-2-hydroxycyclohexanone—85, 4-tert.butylcyclohexanediol-1,2—10, phenol—5. The conversion of the feedstock is 90%, selectivity and productivity for 4-tert.butyl-2-hydroxycyclohexanone are 94.4% and 0.99 kg/l.hr respectively.

EXAMPLE 13

Use is made of the reduced catalyst prepared as described in Example 6 hereinbefore. The reduced catalyst (3 ml) is heated in a stream of carbon dioxide to the temperature of 220° C. and catalytic dehydrogenation of cyclohexanedione-1,2 is carried out. The liquid feedstock is supplied into the reactor at the rate of 0.8 kg/l.hr, the feed rate of carbon dioxide is 53 m³/l.hr, the partial pressure of the feedstock is 0.003 atm.

The reaction mixture is condensed in two traps at the temperature of −20° and 20° C. respectively. The chromatographic analysis of the catalysate is carried out at the column temperature of 140° C. According to the data of the analysis, the catalysate consists of the following components, percent by weight: pyrocatechol—80, phenol—5 and cyclohexanedione-1,2—15. The conversion of the feedstock is 85%, selectivity and productivity for pyrocatechol are 94% and 0.64 kg/l.hr respectively.

EXAMPLE 14

Use is made of the reduced catalyst prepared as described in Example 1. The reduced catalyst (3 ml) is heated in a stream of nitrogen to the temperature of 180° C. and catalytic dehydrogenation of 3-methylcyclohexanol is carried out. The liquid feedstock is supplied into the reactor at the rate of 2.3 kg/l.hr, the feed rate of nitrogen is 6.7 m³/hr, partial pressure of 3-methylcyclohexanol is 0.067 atm.

The reaction mixture is condensed in two traps at the temperature of −20° and 20° C. Chromatographic analysis of the catalysate is conducted at the column temperature of 120° C. According to the data of this analysis, the catalysate consists of the following components, percent by weight: 3-methylcyclohexanone—80, 3-methylcyclohexanol—20. The conversion of the feedstock is 80%, selectivity and productivity relative to 3-methylcyclohexanone are 100% and 1.84 kg/l.hr respectively.

EXAMPLE 15

Use is made of the catalyst prepared as described in Example 9 consisting of the following components, percent by weight:

| nickel | 41 |
|---|---|
| lead | 4.5 |
| kieselguhr | 54.49 |
| sodium sulphide | 0.01. |

The atomic ratio between nickel and lead is 32:1.

The reduced catalyst (5 ml) is heated to the temperature of 300° C. in a stream of nitrogen and catalytic dehydrogenation of cyclohexanediol-1,2 is carried out. The feedstock is supplied into the reactor (as a 10% aqueous solution) at the rate of 1.16 kg/l.hr, the solution feed rate is 11.6 kg/l.hr. The partial pressure of the feedstock is 0.17 atm. The process is carried out continuously for 400 hours, while periodically taking samples of the liquid catalysate from a trap cooled to the temperature of 0° C. The catalysate is analyzed chromatographically at a column temperature of from 110° to 150° C. (programmed heating). According to the data of this analysis of a sample taken at the 6th hour of the catalyst run, the catalysate consists of the following components, percent by weight: pyrocatechol—96, phenol—4. The catalysate composition obtained at the 400th hour of the catalyst run is as follows, percent by weight: pyrocatechol—95, phenol—5. The conversion of cyclohexanediol-1,2 is 100%, selectivity and productivity for pyrocatechol are 95–96% and 1.1 kg/l.hr respectively. Separation of pyrocatechol from the catalysate comprising an aqueous solution of organic substances is effected by means of a double extraction with butanol taken in the equal amount with respect to the catalysate volume. After distilling-off the solvent from the extract pyrocatechol is obtained having purity of 99% and b.p. and m.p. values equal to those known from the literature.

What is claimed is:

1. A catalyst comprising by weight:
nickel 15 to 55%
promotor selected from the group consisting of germanium, lead and mixtures thereof:

| | 0.2 to 8.0% |
|---|---|
| inert carrier | 84.8 to 37.0% | the atomic ratio of nickel to the promoter being from 15:1 to 410:1.

2. A catalyst according to claim 1 further comprising a salt of a metal selected from alkali metals and alkaline earth metals and a mineral acid in an amount of from 0.01 to 1.0% by weight.

3. A catalyst according to claim 2 wherein said alkaline earth metal salt is a calcium or barium salt.

* * * * *